United States Patent
Sun et al.

(10) Patent No.: US 9,309,226 B2
(45) Date of Patent: Apr. 12, 2016

(54) CRYSTALLINE FORM I OF TYROSINE KINASE INHIBITOR DIMALEATE AND PREPARATION METHODS THEREOF

(71) Applicant: Jiangsu Hengrui Medicine Co., Ltd., Lianyungang (CN)

(72) Inventors: Piaoyang Sun, Jiangsu (CN); Guaili Wu, Jiangsu (CN); Bo Yuan, Jiangsu (CN); Yongjiang Chen, Jiangsu (CN)

(73) Assignee: Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 14/412,762

(22) PCT Filed: Jun. 4, 2013

(86) PCT No.: PCT/CN2013/076717
§ 371 (c)(1),
(2) Date: Jan. 5, 2015

(87) PCT Pub. No.: WO2014/008794
PCT Pub. Date: Jan. 16, 2014

(65) Prior Publication Data
US 2015/0166511 A1  Jun. 18, 2015

(30) Foreign Application Priority Data
Jul. 12, 2012 (CN) .......................... 2012 1 0240697

(51) Int. Cl.
C07D 401/14  (2006.01)
C07C 55/08  (2006.01)

(52) U.S. Cl.
CPC .............. *C07D 401/14* (2013.01); *C07C 55/08* (2013.01); *C07B 2200/13* (2013.01)

(58) Field of Classification Search
None
See application file for complete search history.

(56) References Cited

FOREIGN PATENT DOCUMENTS

| CN | 101824029 A | 9/2010 |
|---|---|---|
| CN | 101918390 A | 12/2010 |
| CN | 102675287 A | 9/2012 |
| WO | 2011/029265 A1 | 3/2011 |

OTHER PUBLICATIONS

Int'l Search Report issued on Sep. 5, 2013 in Int'l Application No. PCT/CN2013/076717.

*Primary Examiner* — Timothy R Rozof
(74) *Attorney, Agent, or Firm* — Panitch Schwarze Belisario & Nadel LLP

(57) ABSTRACT

Provided are crystalline Form I of (R,E)-N-(4-(3-chloro-4-(pyridin-2-yl-methoxy)-phenylamino)-3-cyano-7-ethoxy-quinolin-6-yl)-3-(1-methylpyrrolidin-2-yl) propenamide dimaleate (called SHR1258 dimaleate for short), preparation methods thereof, and pharmaceutical compositions containing the same. The crystalline Form I of SHR1258 dimaleate has good crystal stability and chemical stability, and can be used in the preparation of medicaments for treating diseases related to EGFR receptor tyrosine kinase or HER-2 receptor tyrosine kinase.

14 Claims, 4 Drawing Sheets

X-ray Diffraction Test Report
SHR1258

Start angle : 2          End angle : 30          Step Size : 02
Scan speed : 8          Integration time : 15          Target : Cu
Tube current and voltage : 40kV 40mA          Slit : 2/4/0.5/0.2

| Number | 2θ | d value | count | Relative intensity | Half-height width | Integration intensity |
|---|---|---|---|---|---|---|
| 1 | 6.280 | 14.062 | 3353 | 81 | 0.400 | 71380 |
| 2 | 6.740 | 13.104 | 4127 | 100 | 0.320 | 70296 |
| 3 | 10.600 | 8.339 | 1170 | 28 | 0.480 | 29897 |
| 4 | 11.580 | 7.635 | 996 | 24 | 0.760 | 40284 |
| 5 | 13.500 | 6.553 | 1557 | 37 | 0.440 | 36470 |
| 6 | 14.900 | 5.941 | 1551 | 37 | 0.600 | 49517 |
| 7 | 15.800 | 5.604 | 1951 | 47 | 0.640 | 66454 |
| 8 | 17.200 | 5.151 | 1494 | 36 | 3.840 | 305391 |
| 9 | 18.260 | 4.854 | 2253 | 54 | 1.400 | 167871 |
| 10 | 18.920 | 4.687 | 1758 | 42 | 7.000 | 654915 |
| 11 | 20.660 | 4.296 | 2129 | 51 | 6.240 | 707113 |
| 12 | 21.140 | 4.199 | 3538 | 85 | 1.440 | 271182 |
| 13 | 22.500 | 3.948 | 2061 | 49 | 9.960 | 1092504 |
| 14 | 22.960 | 3.870 | 2156 | 52 | 10.840 | 1243343 |
| 15 | 24.340 | 3.654 | 2584 | 62 | 5.080 | 696513 |
| 16 | 25.540 | 3.485 | 3017 | 73 | 4.320 | 693661 |
| 17 | 26.120 | 3.409 | 2257 | 54 | 17.120 | 2056406 |
| 18 | 27.220 | 3.273 | 1693 | 41 | 23.720 | 2137625 |
| 19 | 28.100 | 3.173 | 1645 | 39 | 25.560 | 2238063 |

X-ray Diffraction Test Report

Start angle : 2   End angle : 30   Step Size : 02
Scan speed : 8   Integration time : 15   Target : Cu
Tube current and voltage : 40kV 40mA   Slit : 2/4/0.5/0.2

| Number | 2θ | d value | count | Relative intensity | Half-height width | Integration intensity |
|---|---|---|---|---|---|---|
| 1 | 2.920 | 30.232 | 897 | 57 | 0.020 | 955 |
| 2 | 4.880 | 18.093 | 686 | 43 | 0.020 | 730 |
| 3 | 5.660 | 15.601 | 649 | 41 | 0.020 | 691 |
| 4 | 8.800 | 10.040 | 546 | 35 | 0.020 | 582 |
| 5 | 10.520 | 8.402 | 549 | 35 | 0.020 | 584 |
| 6 | 12.500 | 7.075 | 597 | 38 | 0.020 | 636 |
| 7 | 13.000 | 6.804 | 617 | 39 | 0.020 | 656 |
| 8 | 13.960 | 6.339 | 763 | 48 | 0.020 | 812 |
| 9 | 14.360 | 6.163 | 749 | 48 | 0.020 | 797 |
| 10 | 14.620 | 6.054 | 817 | 52 | 0.020 | 870 |
| 11 | 15.360 | 5.764 | 896 | 57 | 11.200 | 534187 |
| 12 | 15.640 | 5.661 | 963 | 61 | 7.560 | 387669 |
| 13 | 16.080 | 5.507 | 1054 | 67 | 6.880 | 385933 |
| 14 | 16.860 | 5.254 | 1151 | 73 | 7.400 | 453343 |
| 15 | 17.520 | 5.058 | 1262 | 80 | 8.690 | 577530 |
| 16 | 18.420 | 4.813 | 1364 | 87 | 8.440 | 612640 |
| 17 | 20.260 | 4.380 | 1451 | 93 | 11.560 | 892396 |
| 18 | 21.020 | 4.223 | 1549 | 99 | 11.880 | 979373 |
| 19 | 21.260 | 4.176 | 1510 | 96 | 13.520 | 1086733 |
| 20 | 22.220 | 3.997 | 1557 | 99 | 14.280 | 1183594 |
| 21 | 23.340 | 3.808 | 1533 | 98 | 16.560 | 1351035 |
| 22 | 23.700 | 3.751 | 1509 | 96 | 18.400 | 1477512 |
| 23 | 23.940 | 3.714 | 1559 | 100 | 17.720 | 1470660 |
| 24 | 25.560 | 3.482 | 1512 | 96 | 22.120 | 1780321 |
| 25 | 25.860 | 3.442 | 1384 | 88 | 23.280 | 1714901 |
| 26 | 26.820 | 3.321 | 1285 | 82 | 27.000 | 1847037 |
| 27 | 27.060 | 3.292 | 1275 | 81 | 27.520 | 1867090 |
| 28 | 27.460 | 3.245 | 1134 | 72 | 29.040 | 1752634 |
| 29 | 28.580 | 3.121 | 1029 | 66 | 33.360 | 1827829 |
| 30 | 28.820 | 3.095 | 945 | 60 | 34.840 | 1753136 |

CRYSTALLINE FORM I OF TYROSINE KINASE INHIBITOR DIMALEATE AND PREPARATION METHODS THEREOF

CROSS-REFERENCE TO RELATED APPLICATIONS

This application is a Section 371 of International Application No. PCT/CN2013/076717, filed on Jun. 4, 2013, which was published in the Chinese language on Jan. 16, 2014, under International Publication No. WO 2014/008794, and the disclosure of which is incorporated herein by reference.

FIELD OF THE INVENTION

The present invention relates to a crystalline form of a tyrosine kinase inhibitor dimaleate, particularly form I crystal of (R, E)-N-(4-(3-chloro-4-(pyridin-2-yl-methoxy)phenylamino)-3-cyano-7-ethoxyquinolin-6-yl)-3-(1-methylpyrrolidino-2-yl)acrylamide dimaleate, and the preparation and use thereof.

BACKGROUND OF THE INVENTION

In recent years, cancer mortality in our country has clearly been on the rise. People's lives and the quality of life are seriously threatened by cancer. Thus, it is a challenging and significant subject to search for new anticancer drugs with high efficacy and low toxicity in the life sciences nowadays. Receptor tyrosine kinase is a kind of transmembrane protein involved in signal transduction. It has been shown that over 50% of the proto-oncogene and oncogene products have tyrosine kinase activity, and their abnormal expression causes tumorigenesis. Tyrosine kinase inhibitors have been approved to be on the market since 2001, which have become a new class of anticancer drugs with good performance.

Epidermal growth factor receptor (EGFR) is a member of the receptor tyrosine kinase family. The epidermal growth factor receptor pathway plays a very important role in tumorigenesis and progression, which has become the main research subject and one of the developing targets in the field of cancer therapy. Such drugs which have been on the market now include erlotinib, gefitinib and lapatinib (Tykerb, GW572016), as well as neratinib, which is currently in the clinical phase. PCT Patent Application Publication WO2011029265 discloses a method for the preparation of the compound (R, E)-N-(4-(3-chloro-4-(pyridin-2-ylmethoxy) phenylamino)-3-cyano-7-ethoxyquino line-6-yl)-3-(1-methylpyrrolidino-2-yl)acrylamide (referred to as "SHR1258" below for convenience). This drug molecule has distinct advantages of pharmacokinetics and pharmacodynamics. Although PCT Patent Application Publication WO2011029265 discloses the chemical structure and preparation method of compound SHR1258, it is silent to the condition of its salification. In Chinese Patent Application No. 201110062359.8, the dimaleate of this compound (referred to as "SHR1258 dimaleate" below) has been described, and its structure is as follows:

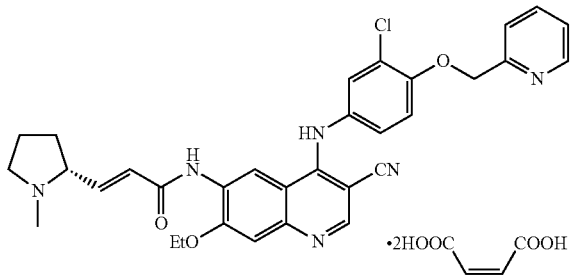

However, the inventors did not do further research on the polymorphs and preparation method of SHR1258 dimaleate. As known to the person skilled in the art, the polymorph structure of the pharmaceutically active ingredient always affects the chemical stability of the drug. Different storage conditions and crystallization conditions may lead to a change in the polymorph structure of the compound, which is sometimes accompanied by other forms of polymorph. In general, an amorphous drug product does not have a regular crystal structure, and often has other defects such as poor product stability, smaller particle size, hard filtration, agglomerates easily, and poor solubility. Thus, it is necessary to improve all aspects of the nature of the above product. There is a need to search for a new polymorph which has higher polymorph purity and better chemical stability.

SUMMARY OF THE INVENTION

The present invention provides a stable crystal form of SHR1258 dimaleate and a preparation method thereof.

The inventor has tested a series of crystallization products of SHR1258 dimaleate obtained under various conditions by X-ray diffraction and differential scanning calorimetry (DSC) tests. The results show that a stable crystal form of SHR1258 dimaleate, which is referred to as form I crystal, can be obtained under normal crystallization conditions. DSC patterns of the present form I crystal of SHR1258 dimaleate show a distinct melting absorption peak at 130° C. The X-ray diffraction pattern is shown in FIG. 1, which used Cu-Kα radiation to obtain the X-ray diffraction patterns represented by 2θ angles and interplanar crystal spacing (d value) in which there are characteristic peaks at 6.28 (14.06), 6.74 (13.10), 10.60 (8.34), 11.58 (7.64), 13.50 (6.55), 14.90 (5.94), 15.80 (5.60), 18.26 (4.85), 20.66 (4.30), 21.14 (4.20), 22.96 (3.87), 24.34 (3.65), 25.54 (3.49), and 26.12 (3.41).

In the method for the preparation of the form I crystal of the present invention, there is no special limitation for the existing form of SHR1258 dimaleate as starting material, and it can be used in any crystal form or amorphous form. A method for the preparation of form I crystal of SHR1258 dimaleate of the present invention comprises the following steps:

When using an organic solvent with a small number of carbon atoms as a crystallization solvent, a polar organic solvent with a small number of carbon atoms and higher volatility is preferred, such as alcohols, ketones, esters, or a mixture thereof; and isopropyl alcohol, acetone, ethanol, ethyl acetate, tetrahydrofuran or a mixture thereof is more preferred for the recrystallization of SHR1258 dimaleate. The solvent for crystallization can be a single solvent or a mixture of solvents comprising the solvents mentioned above.

Specifically, the process for the preparation of form I crystal of SHR1258 dimaleate comprises the following steps:
(1) A mixture of SHR1258 and maleic acid or the SHR1258 dimaleate solid is dissolved in a sufficient quantity of organic solvents, and the solution obtained is cooled to cause crystallization.
(2) The crystals are filtered, washed, and dried.

In a preferred embodiment of the present invention, the organic solvent in step 1 is selected from one or more solvents of alcohols with no more than three carbons, acetone, ethyl esters, and tetrahydrofuran, preferably ethanol, isopropyl alcohol, and tetrahydrofuran.

Furthermore, the most preferred single solvent is isopropyl alcohol.

In another embodiment of the present invention, the preferred mixture of solvents is a mixture of ethanol and tetrahydrofuran. The ratio of the two is not limited, while the volume ratio of 1:1 is preferred in an embodiment of the present invention.

The recrystallization method is not limited and can be performed with conventional recrystallization processes used in the art. For example, SHR1258 dimaleate can be heated to dissolve in organic solvent, and then the solution is cooled gradually and let stand to crystallize, or the solution is stirred to crystallize. After crystallization, the resulting precipitate is collected by filtration and then dried. In particular, a full conversion process is necessary for the formation of the stable crystal form, and an amorphous structure or crystals with lower purity will form easily when the crystallization process is too fast, which is usually caused by a supersaturated solution. An increase in solvent volume or a decrease in crystallization rate will be helpful for the formation of a stable crystal form with high purity. The crystals obtained by filtration are usually dried under vacuum at about 30° C. to 100° C., preferably 40° C. to 60° C., to remove the recrystallization solvent.

The resulting crystal form of SHR1258 dimaleate was determined by DSC and X-ray diffraction patterns. Meanwhile, the residual solvent was also determined.

The crystal of SHR1258 dimaleate prepared according to the present method has no or very little residual solvent, which meets the requirement of the national pharmacopoeia for the residual solvent of drug products. Thus, the crystal of the present invention can be properly used as a pharmaceutical active ingredient.

The research results show that the stability of the form I crystal of SHR1258 dimaleate obtained in the present invention is significantly better than the amorphous form under the conditions of high temperature and high humidity. Moreover, the form I crystal has good stability under the conditions of grinding, pressure and heating, which can meet the production, transportation, and storage requirements of medicaments. The preparation process is stable and repeatable, which is especially suitable for industrial production.

DETAILED DESCRIPTION OF THE INVENTION

The present invention is illustrated by the following examples in detail, which in no way should be construed as limiting the scope of the present invention.

Experimental instruments 1. Thermal analysis (DSC)
Instrument type: Perkin-Elmer Pyris 1 Series Thermal Analysis System
Purging gas: Nitrogen
Heating rate: 10.0° C./min
Temperature range: 50-300° C.
2. X-ray diffraction spectrum
Instrument type: D/Max-RA Japan rigaku X-ray powder diffraction
Ray: monochromatic Cu—Kα rays (λ=1.5418 Å)
Scanning mode: θ/2θ, Angular scan of 2-40°
Voltage: 40 KV
Electric Current: 40 mA

EXAMPLE 1

Figure 1:
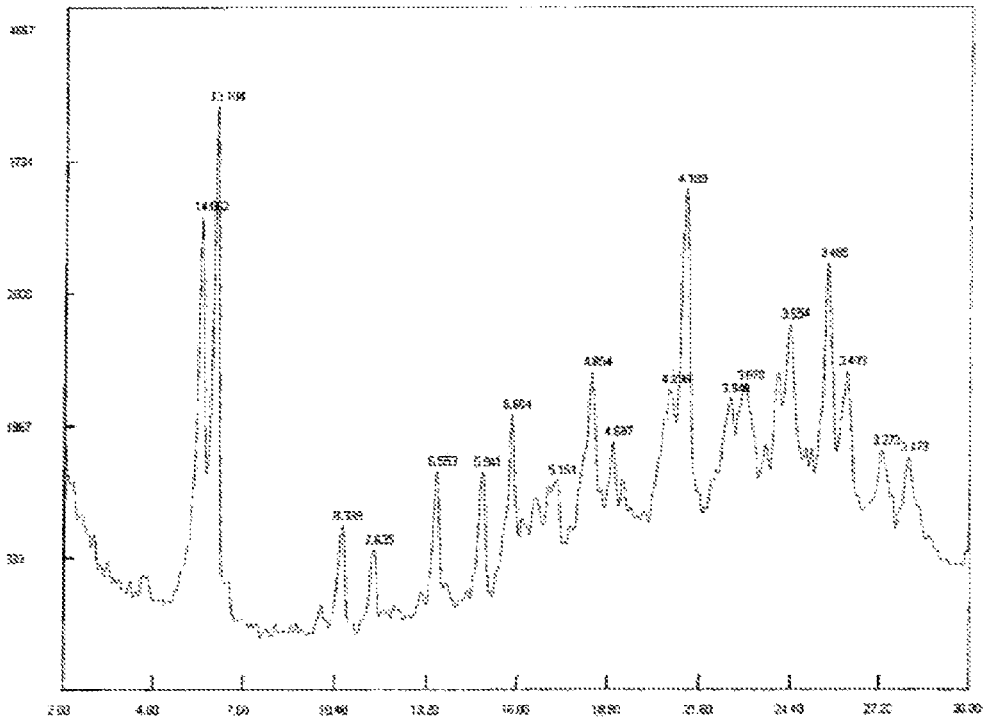
FIG. 1 shows the X-ray powder diffraction pattern for the form I crystal of SHR1258 dimaleate.
Figure 2:
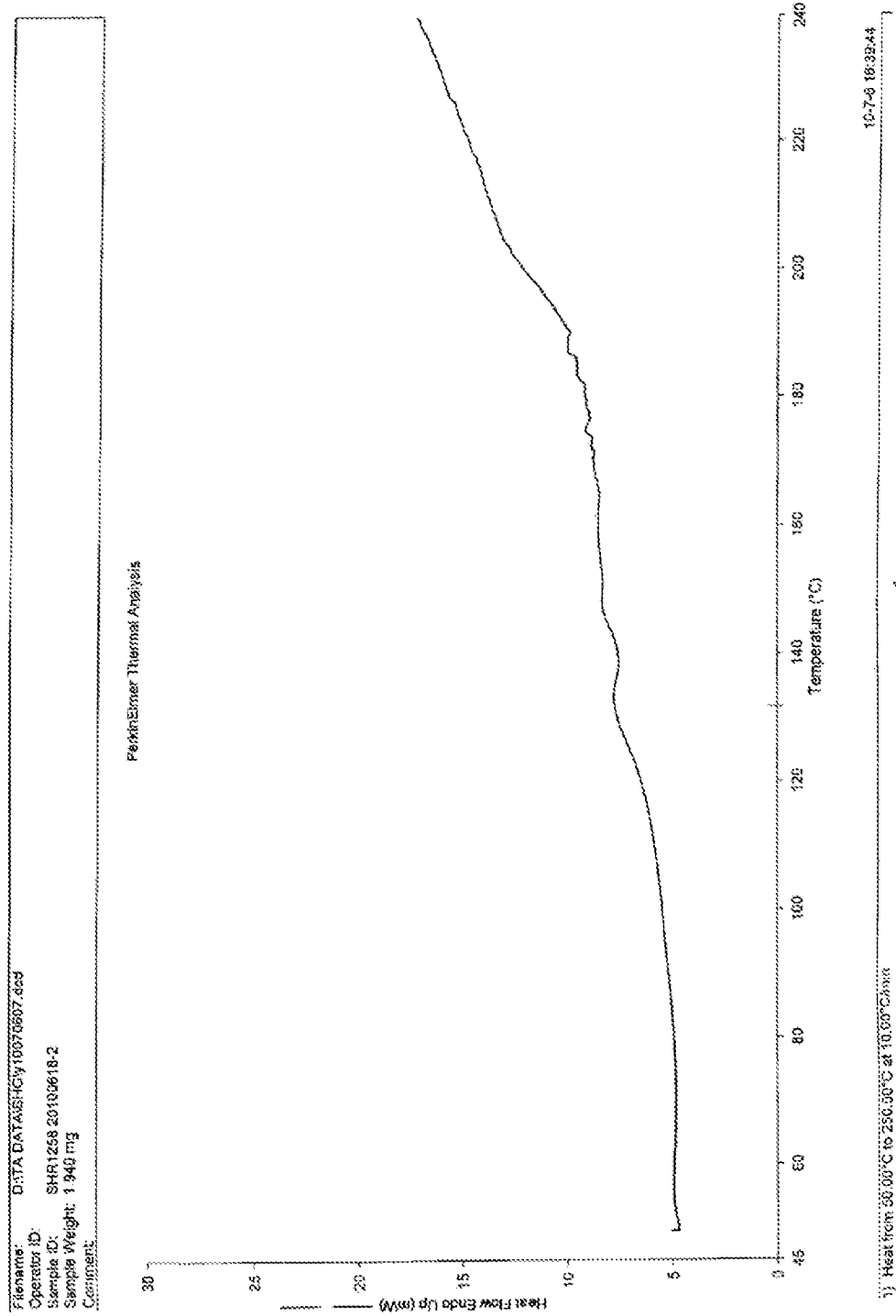
FIG. 2 shows the Differential Scanning Calorimetry pattern for the form I crystal of SHR1258 dimaleate.

1.0 g of SHR1258 (prepared according to PCT Patent Application Publication WO2011029265) and 0.4 g of maleic acid were dissolved in 25 ml of isopropyl alcohol by heating. A solid was present while refluxing. After removing from heating, the obtained mixture was stirred to cause a precipitate. The resulting precipitate was collected by filtration and then dried at 45° C. under vacuum overnight to obtain 0.85 g of SHR1258 dimaleate crystal. Yield: 60%. X-ray diffraction pattern is shown in FIG. 1 in which there are characteristic peaks at 6.28 (14.06), 6.74 (13.10), 10.60 (8.34), 11.58 (7.64), 13.50 (6.55), 14.90 (5.94), 15.80 (5.60), 18.26 (4.85), 20.66 (4.30), 21.14 (4.20), 22.96 (3.87), 24.34 (3.65), 25.54 (3.49), and 26.12 (3.41). The DSC pattern is shown in FIG. 2, with a sharp heat absorption peak at 131.429° C. The crystal was defined as form I crystal.

EXAMPLE 2

Figure 3:
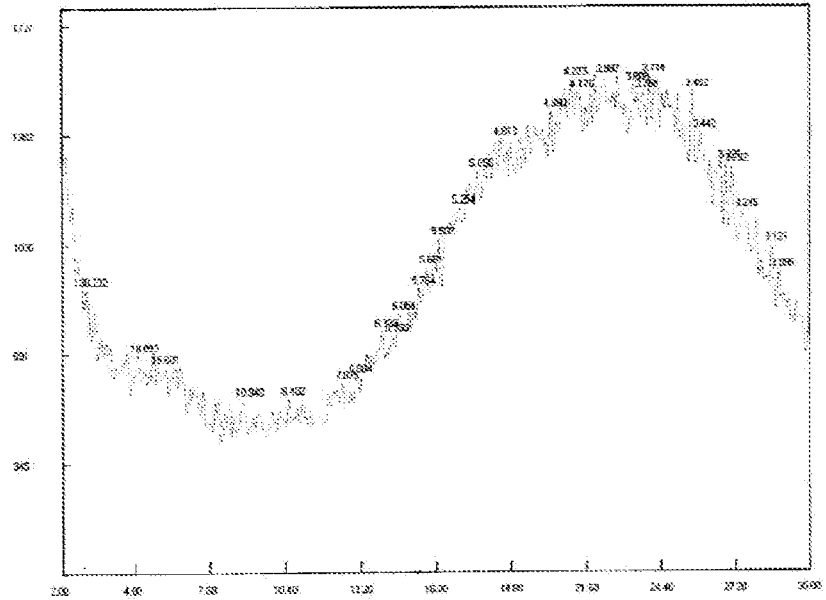
FIG. 3 shows the X-ray powder diffraction pattern for an amorphous form of SHR1258 dimaleate.
Figure 4:
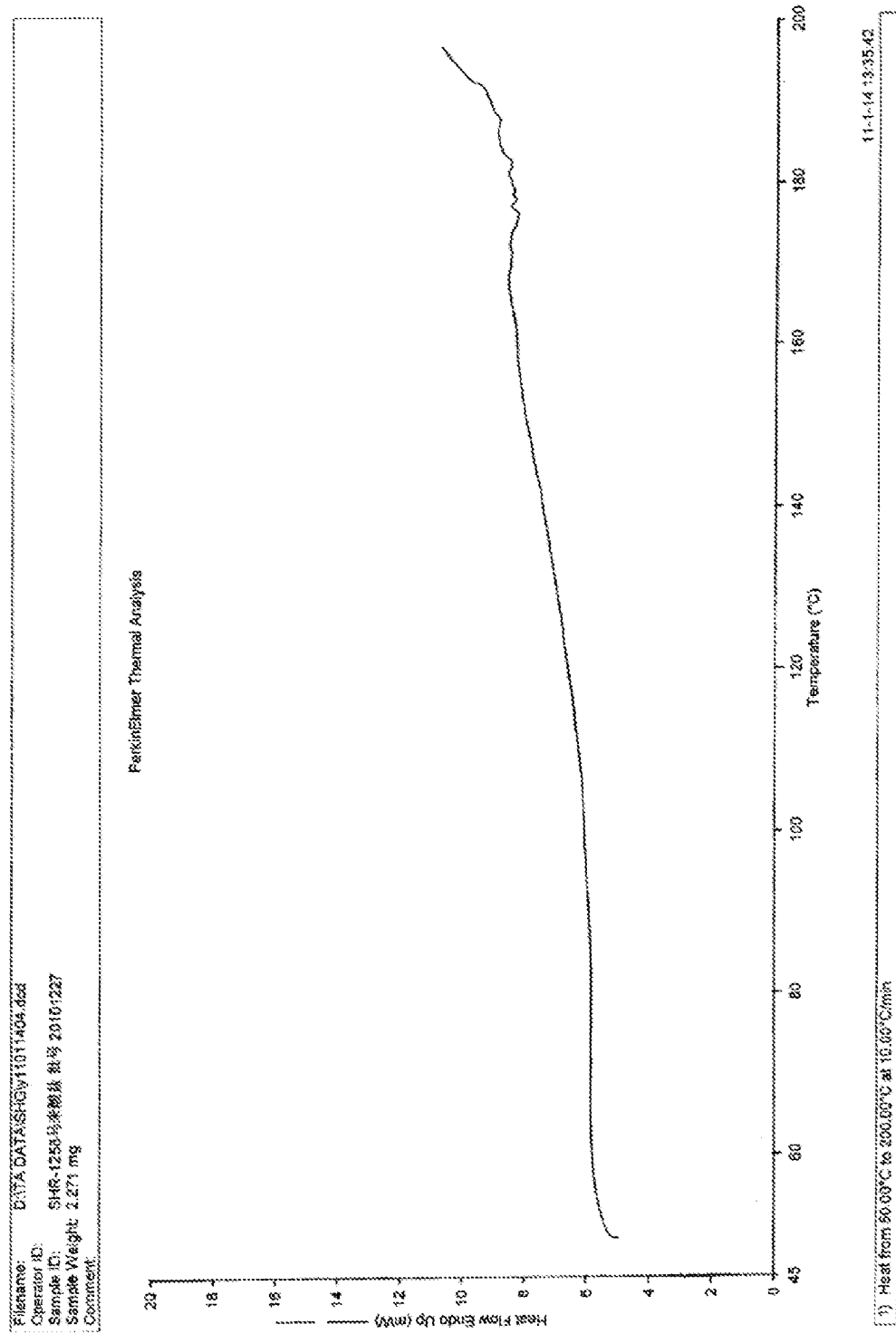
FIG. 4 shows the Differential Scanning Calorimetry pattern for an amorphous form of SHR1258 dimaleate.

1.0 g of SHR1258 and 0.4 g of maleic acid were dissolved in 20 ml of ethanol by heating. After removing from heating, the mixture was stirred overnight (the solid that separated was sticky). The next day, 30 ml of diethyl ether were added to the mixture and stirred. The resulting precipitate was collected by filtration, washed with diethyl ether and then dried to obtain 1.03 g of yellow solid. Yield: 73.5%. X-ray diffraction pattern of this solid is shown in FIG. 3 in which there are no characteristic peaks. The DSC pattern is shown in FIG. 4, with no heat absorption peak below 170° C. It was determined that the product was an amorphous form.

EXAMPLE 3

1.0 g of SHR1258 dimaleate (prepared according to example 2) was added to 5 ml of methanol and the mixture was heated to reflux until a solution was obtained. The solvent was removed by evaporation under vacuum, and 20 ml of isopropyl alcohol were added. The solid was dissolved completely by heating, and some solid was present while refluxing. After removing from heating, the mixture was left to cause crystallization. The precipitate was collected by filtration and dried to obtain 0.80 g solid. Yield: 80.0%. It was determined to be form I crystal of SHR1258 dimaleate after comparing the X-ray diffraction patterns and DSC patterns.

EXAMPLE 4

2.0 g of SHR1258 and 0.8 g of maleic acid were heated to dissolve in 26 ml of ethanol and tetrahydrofuran mixture (at a volume ratio of 1:1). The solution was stirred in a 45° C. water bath with solid separated. After removing from heating, the mixture was stirred to cause crystallization. The precipitate was collected by filtration and dried at 45° C. under vacuum overnight to obtain 2.3 g of crystal. Yield: 82.0%. It was determined to be form I crystal of SHR1258 dimaleate after comparing the X-ray diffraction patterns and DSC patterns.

EXAMPLE 5

1.0 g of SHR1258 dimaleate solid (prepared according to Example 2) was added to 5 ml of water. The mixture was heated to reflux until a solution was obtained. The solution was stirred to cause as precipitate, and a sticky solid appeared the next day. The precipitate was collected by filtration and dried to obtain 0.68 g solid. Yield: 68.3%. It was determined to be an amorphous form of SHR1258 dimaleate from the X-ray diffraction patterns and DSC patterns.

EXAMPLE 6

The form I crystal of SHR1258 dimaleate prepared in Example 1 and the amorphous form of SHR1258 dimaleate prepared in Example 2 were placed open in the air to test the stability in various conditions including illumination (4500 Lux), heating (60° C.), and humidity (RH 90%). The investigation duration was five and ten days, and the HPLC analysis results are shown in Table 1.

TABLE 1

Comparing the stability of form I crystal and amorphous form crystal of SHR1258 dimaleate

| Bach number | Solvent | Time (Day) | Light | 60° C. | RH 90% |
|---|---|---|---|---|---|
| Form I Crystal | Isopropyl Alcohol | 0 | 99.65% | 99.65% | 99.65% |
| | | 5 | 98.20% | 98.13% | 98.35% |
| | | 10 | 97.91% | 96.86% | 98.35% |
| Amorphous Form | 95% Ethyl Alcohol | 0 | 98.41% | 98.41% | 98.41% |
| | | 5 | 96.96% | 95.24% | 96.95% |
| | | 10 | 96.91% | 93.71% | 96.31% |

The form I crystal of SHR1258 dimaleate and the amorphous form of SHR1258 dimaleate were placed open in the air in various conditions including illumination, heating, and humidity. The results show that the stability of the form I crystal of SHR1258 dimaleate and amorphous form of SHR1258 dimaleate are similar under illumination without any statistically significant difference. The form I crystal of SHR1258 dimaleate is more stable than amorphous SHR1258 dimaleate under high temperature and high moisture conditions.

EXAMPLE 7

The form I crystal of SHR1258 dimaleate prepared in Example 1 was grinded, heated and pressed, then evaluated by X-ray diffraction and DSC patterns. The results show that the crystal is stable and the data is shown in Table 2.

TABLE 2

| Batch number | Process | Experiment process | Crystal | DSC |
|---|---|---|---|---|
| Experiment 7.1 S0915100402G | Grinding for 10 min | 1.0 g of form I crystal of SHR1258 dimaleate was grinded for 10 min to mortar under nitrogen atmosphere. | Form I | DSC peak: 130.716° C. |
| Experiment 7.2 S0915100402H | Heating at 80° C. for 3 hours | 1.0 g of form I crystal of SHR1258 dimaleate was spread and heated at 80° C. for 3 hours | Form I | DSC peak: 133.588° C. |
| Experiment 7.3 S0915100402P | Pressing | Pressing the form I crystal of SHR1258 dimaleate into pieces | Form I | DSC peak: 131.726° C. |

What is claimed is:

1. A form I crystal of (R,E)-N-(4-(3-chloro-4-(pyridin-2-ylmethoxy)-phenylamino)-3-cyano-7-ethoxyquinolin-6-yl)-3-(1-methylpyrrolidin-2-yl) acrylamide dimaleate, wherein using Cu—Kα radiation to obtain an X-ray diffraction pattern represented by 2θ angle (interplanar crystal spacing), the form I crystal has the X-ray diffraction pattern comprising characteristic peaks at 6.28 (14.06), 6.74 (13.10), 10.60 (8.34), 11.58 (7.64), 13.50 (6.55), 14.90 (5.94), 15.80 (5.60), 18.26 (4.85), 20.66 (4.30), 21.14 (4.20), 22.96 (3.87), 24.34 (3.65), 25.54 (3.49), and 26.12 (3.41).

2. A method for preparing the form I crystal of (R,E)-N-(4-(3-chloro-4-(pyridin-2-ylmethoxy)-phenylamino)-3-cyano-7-ethoxyquinolin-6-yl)-3-(1-methylpyrrolidin-2-yl) acrylamide dimaleate according to claim 1, the method comprising the following steps:
   1) heating a mixture of any crystal form or amorphous form of (R,E)-N-(4-(3-chloro-4-(pyridin-2-ylmethoxy)-phenylamino)-3-cyano-7-ethoxyquinolin-6-yl)-3-(1-methylpyrrolidin-2-yl)acrylamide and maleic acid, or a solid of any crystal form or amorphous form of (R,E)-N-(4-(3-chloro-4-(pyridin-2-ylmethoxy)-phenylamino)-3-cyano-7-ethoxyquinolin-6-yl)-3-(1-methylpyrrolidin-2-yl)acrylamide dimaleate, in a sufficient quantity of organic solvent to dissolve the crystal form or amorphous form or the solid of any crystal form or amorphous form to obtain a solution, then cooling the solution to cause crystallization; said organic solvent is one or more of a solvent selected from the group consisting of alcohols with no more than three carbons, acetone, ethyl acetate, and tetrahydrofuran; and
   2) filtering, washing, and drying the crystals obtained in step (1).

3. The method according to claim 2, wherein the organic solvent in step (1) is isopropyl alcohol.

4. The method according to claim 2, wherein the organic solvent in step (1) is a mixture of solvents of ethanol and tetrahydrofuran.

5. A pharmaceutical composition comprising the form I crystal of (R,E)-N-(4-(3-chloro-4-(pyridin-2-ylmethoxy)-phenylamino)-3-cyano-7-ethoxyquinolin-6-yl)-3-(1-methylpyrrolidin-2-yl)acrylamide dimaleate according to claim 1 and a pharmaceutically acceptable carrier.

6. The method according to claim 2, wherein the organic solvent is selected from the group consisting of ethanol, isopropyl alcohol, tetrahydrofuran, and mixtures thereof.

7. A method of treating cancer, the method comprising administering the pharmaceutical composition according to claim 5 to a subject in need of treatment thereof, wherein the cancer is selected from the group consisting of lung cancer, breast cancer, epidermal squamous carcinoma and gastric cancer.

8. The form I crystal of (R,E)-N-(4-(3-chloro-4-(pyridin-2-ylmethoxy)-phenylamino)-3-cyano-7-ethoxyquinolin-6-yl)-3-(1-methylpyrrolidin-2-yl) acrylamide dimaleate according to claim 1, having the X-ray diffraction pattern of FIG. 1.

9. A method for preparing the form I crystal of (R,E)-N-(4-(3-chloro-4-(pyridin-2-ylmethoxy)-phenylamino)-3-cyano-7-ethoxyquinolin-6-yl)-3-(1-methylpyrrolidin-2-yl) acrylamide dimaleate according to claim 8, the method comprising:
   1) heating a mixture of any crystal form or amorphous form of (R,E)-N-(4-(3-chloro-4-(pyridin-2-ylmethoxy)-phenylamino)-3-cyano-7-ethoxyquinolin-6-yl)-3-(1-methylpyrrolidin-2-yl)acrylamide and maleic acid, or a solid of any crystal form or amorphous form of (R,E)-N-(4-(3-chloro-4-(pyridin-2-ylmethoxy)-phenylamino)-3-cyano-7-ethoxyquinolin-6-yl)-3-(1-methylpyrrolidin-2-yl)acrylamide dimaleate, in a sufficient quantity of organic solvent to dissolve the crystal form or amorphous form or the solid of any crystal form or amorphous form to obtain a solution, then cooling the solution to cause crystallization; said organic solvent is one or more of a solvent selected from the group consisting of alcohols with no more than three carbons, acetone, ethyl acetate, and tetrahydrofuran; and 2) filtering, washing, and drying the crystals obtained in step (1).

10. The method according to claim 9, wherein the organic solvent in step (1) is isopropyl alcohol.

11. The method according to claim 9, wherein the organic solvent in step (1) is a mixture of solvents of ethanol and tetrahydrofuran.

12. The method according to claim 9, wherein the organic solvent is selected from the group consisting of ethanol, isopropyl alcohol, tetrahydrofuran, and mixtures thereof.

13. A pharmaceutical composition comprising the form I crystal of (R,E)-N-(4-(3-chloro-4-(pyridin-2-ylmethoxy)-phenylamino)-3-cyano-7-ethoxyquinolin-6-yl)-3-(1-methylpyrrolidin-2-yl)acrylamide dimaleate according to claim 8 and a pharmaceutically acceptable carrier.

14. A method of treating cancer, the method comprising administering the pharmaceutical composition according to claim 13 to a subject in need of treatment thereof, wherein the cancer is selected from the group consisting of lung cancer, breast cancer, epidermal squamous carcinoma and gastric cancer.

* * * * *